United States Patent
Garvey (10) Patent No.: US 7,454,050 B2
(45) Date of Patent: Nov. 18, 2008

(54) METHOD OF AUTOMATING A THERMOGRAPHIC INSPECTION PROCESS

(75) Inventor: Raymond E. Garvey, Loudon, TN (US)

(73) Assignee: CSI Technology, Inc., Wilmington, DE (US)

( * ) Notice: Subject to any disclaimer, the term of this patent is extended or adjusted under 35 U.S.C. 154(b) by 677 days.

(21) Appl. No.: 10/872,041

(22) Filed: Jun. 18, 2004

(65) Prior Publication Data
US 2005/0281456 A1 Dec. 22, 2005

(51) Int. Cl.
G06K 9/00 (2006.01)
(52) U.S. Cl. ............ 382/141; 374/121; 374/124; 250/332
(58) Field of Classification Search ........... 382/135, 382/141, 168, 143, 149, 152; 348/135, 84, 348/E5.09, 125, E7.086, E5.029, E5.047, 348/86; 351/206; 156/64, 73.1; 356/237.1, 356/256; 700/108, 95, 212; 374/5, 10, 120, 374/121, 124; 250/330, 332, 358.1, 341.6, 250/339.02, 339.14, 341.1; 209/577
See application file for complete search history.

(56) References Cited

U.S. PATENT DOCUMENTS

| 5,386,117 | A | 1/1995 | Piety et al. |
| 5,637,871 | A | 6/1997 | Piety et al. |
| 6,249,311 | B1 * | 6/2001 | Rouse et al. ............... 348/164 |
| 6,447,460 | B1 | 9/2002 | Zheng et al. |
| 6,516,084 | B2 | 2/2003 | Shepard |
| 6,606,115 | B1 | 8/2003 | Alicandro et al. |
| 6,665,004 | B1 * | 12/2003 | Paff ............................ 348/156 |
| 2004/0159789 | A1 * | 8/2004 | Treado et al. ............. 250/339.07 |
| 2005/0008215 | A1 * | 1/2005 | Shepard ..................... 382/141 |

OTHER PUBLICATIONS

Internet Article from Emerson Process Management entitled Hot Times #2, Substation Component Information for Infrared Thermographers by John Giesecke (11 pages), Nov. 20, 2003.
Internet Article from FLIR Systems entitled ThermaCAM™ Researcher HS—With Computer for FLIR Infrared Camera Systems (2 pages), Jun. 19, 2002.
Internet Article from FLIR Systems entitled PC-Card™ Interface for FLIR infrared camera systems (2 pages), Apr. 27, 2004.
Article from FLIR Systems entitled ThermaCAM® Reporter™, Jan. 1, 2002.

* cited by examiner

*Primary Examiner*—Sheela C Chawan
(74) *Attorney, Agent, or Firm*—Luedeka, Neely & Graham, P.C.

(57) ABSTRACT

A process for using a hand-held infrared inspection system incorporating on-board training, on-board validation, on-board operator certification, on-board reporting information, or on-board survey instructions. Improved methods for automating area surveys are provided through exception-driven surveillance practices. Imbedded information enables less experienced operators to use more sophisticated devices more effectively. Validation or certification assures operator knowledge or ability. Multilevel classification of anomalies aids in automated analysis and report generation.

5 Claims, 8 Drawing Sheets

Figure 1

LIGHTNING ARRESTERS

Lightening Arrester Function: Lightning arresters (LA's) protect electrical equipment from ......

Lightening Arrester Unique Characteristics: Physically, LA's look similar to a standoff insulator, but ......

IR Analysis: The normal thermal signature is ambient. The most common IR anomaly is .......

Figure 2

LOAD TAP CHANGER (LTC)

Load Tap Changer Function: As the system load changes, the load tap changer (LTC) changes ......

Load Tap Changer Unique Characteristics: An LTC is a set of movable and stationary contacts that are ............

Load Tap Changer IR Analysis: Any heat present in the LTC compartment is conducted through ......

Figure 3

TRANSFORMER COOLING SYSTEM

Transformer Cooling System Function: To maintain .....

Transformer Cooling System Unique Characteristics: There are several different cooling system configurations...........

Transformer Cooling System IR Analysis: Approximately 70% of the cooling takes place in the top one-third of ................

Figure 4

Inspection Requirements
❏ Safety training
❏ Operator certification
❏ Lock-out/Tag-out
❏ Inspect A
❏ Inspect B
❏ Etc.

Checklist
❏ Task A
❏ Task B
❏ Etc.

METHOD OF AUTOMATING A THERMOGRAPHIC INSPECTION PROCESS

FIELD

This invention relates to the field of inspection of persons, animals, areas, facilities, machinery and equipment for diagnosis and treatment in the case of persons and animals, and surveillance in the case of areas, and trouble-shooting, repair and preventive maintenance in the case of facilities and equipment. More particularly, this invention relates to infrared camera and other camera inspection systems used for these purposes.

BACKGROUND

The visual inspection of persons, animals, machinery, and equipment and the general surveillance of areas and facilities is sometimes supplemented by the use of cameras that detect infrared spectra and provide a visible image of the field of view. Some of these cameras provide more detailed thermal information and are called thermographic imaging systems. Many of these cameras are hand-held, and incorporate microprocessors with on-board digital memory to capture and record images. Often the camera has an interface to a laptop computer which provides additional data management and storage capability. The visible image provided by thermographic imaging systems depicts relative temperatures of observed objects, typically with red tones being used to portray higher temperatures and blue tones used to portray lower temperatures. Thus when viewing machinery and equipment the image provides information about the operating condition of the machinery and equipment. However, in order to acquire data that are meaningful for inspection and maintenance of machinery and equipment it is important that the camera be properly adjusted and that appropriate images be observed and recorded by the operator. Improper camera settings, failure to check important machinery features, and mistakes in recording inspection results occur frequently enough to cause significant problems in the implementation of current technology. Thus, there is a need for better operator training, improved inspection processes, and more effective data recording techniques when deploying these cameras for commercial inspection applications.

SUMMARY

In the present invention a method is defined for directing an inspection process using a programmable infrared camera. The method includes loading the programmable infrared camera with an inspection training application software routine. The inspection training application software routine describes at least one aspect of the inspection process. The method further includes running the inspection training application software routine to provide training information to an operator regarding how to perform at least one aspect of the inspection process.

Also defined is a method for directing an inspection process using a programmable infrared camera where the method includes loading the programmable infrared camera with an operator validation application software routine, where the operator validation application software routine incorporates at least one validation question associated with at least one aspect of the inspection process. The method further includes running the operator validation application software routine to pose at least one validation question to the operator and using the programmable infrared camera to indicate the operator's response to at least one posed validation question.

In a further embodiment, a method for directing an inspection process using a programmable camera is established where the method includes loading the camera with a survey results application software routine where the survey results application software routine defines at least one finding for at least one aspect of the inspection process in terms of multi-vector representation of a plurality of dissimilar classifications and defines a plurality of grading levels for at least one classification. The method also includes running the survey results application software routine to assign at least one grading level to at least one of the classifications of at least one of the findings.

Yet another embodiment defines a different method for directing an inspection process using a programmable infrared camera. This method includes loading the programmable infrared camera with a survey template application software routine where the survey template application software routine describes at least one aspect of the inspection process. The method continues by running the survey template application software routine to instruct an operator to inspect the vicinity of an area and to guide the operator through the at least one aspect of the inspection process.

In another aspect the invention provides an infrared inspection camera for conducting an inspection process, where the camera includes a housing, a lens mounted in an opening in the housing, and an infrared focal plane array mounted in the housing in a position to receive infrared radiation from the lens. A microprocessor is mounted in the housing and connected to the infrared focal play array for receiving image data from the focal plane array. An input device is also operatively connected to the microprocessor to accept input data from an operator. A data storage memory is operatively connected to the microprocessor, the data storage memory for storing operator proficiency application software that provides training information, for recording image data received by the microprocessor from the infrared focal plane array, for storing image data from the microprocessor, and for storing input from the input device. A display is operatively connected to the microprocessor for displaying the image data, the training information, and the input data to the operator. A power distribution system provides power. The infrared inspection camera also includes a microprocessor operating system installed in the microprocessor for controlling the flow of data between the microprocessor and (a) the infrared focal plane array, (b) the data storage memory, (c) the display, and (d) the input device under the direction of the operator proficiency application software.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

The automated thermographic inspection process expands the art for infrared inspection processes. Through the use of automation, less skilled and less well trained operators are able to use more sophisticated and more capable infrared inspection systems used by inspectors, technicians, security personnel, engineers, and others who depend on infrared imaging for thermography or surveillance other inspections used to discern, differentiate, or identify characteristics revealed by temperature and/or emissivity variations in equipment, machinery, animals, people, or other substances.

In the most preferred embodiments, the process involves the use of a portable programmable focal plane array infrared (IR) camera that includes an un-cooled radiometric infrared focal plane array plus visible camera built into a lightweight, hand-held package with onboard data storage memory, a Liquid Crystal Display (LCD) or similar display for displaying image data, a microprocessor, a microprocessor operating system, and an interactive user interface that includes an input device for accepting operator input data.

In many embodiments the input device is a "thumb-mouse" mounted on the camera body. The thumb-mouse has a button that can be tilted in a plurality of directions, and input selections can be triggered by depressing the button. In other embodiments the input device is merely an "A or B" position switch or touch screen or touch pad or similar functioning user interface device. In some embodiments the input device is a keyboard that is either integral to the camera or attached externally. The input device is used to collect an operator's response to a prompt made by the application software. The prompt may be a visual or audio cue such as a question or a list of alternative actions, and the types of responses include bimodal (yes/no, true/false, etc.) responses, multiple choice (A, B, C, or D) responses, and free form text or numerical responses. In preferred embodiments, information regarding the response is recorded in the on-board data storage memory and includes identification of the prompt and identification of the response. These interactive features provide support for the operator that is customized for his/her needs and are designed to accommodate the specific requirements of a particular inspection process.

This portable programmable focal plane array infrared camera system may be used in conjunction with an external station, such as a desktop personal computer, a workstation, or a server on which software resides for managing information transmitted to and from the portable imaging system.

Preferably, operator proficiency application software is also installed on the portable camera. Examples of operator proficiency application software are inspection training application software routines, operator validation application software routines, survey template application software routines, and survey results application software routines, each of which will subsequently be described in detail. The operator proficiency application software may be permanently installed in the camera from the factory, or it may be uploaded from a software repository such as a base workstation or an internet web site. The applications software may also be uploaded "live" and displayed on the camera display, preferably using a thin client application with a wired or wireless connection. This process of uploading is typically done by the operator or an inspection supervisor. Preferably, an interface program is installed with the software repository or the "live" software source, such that the application software that is required for a specific inspection process is identified and uploaded automatically based upon input provided to the interface program software The application software is often used to assist the operator in performing various inspection processes in the field. These inspection processes include analyzing, diagnosing, prompting, assisting with fault or equipment information, integrating images from a visible camera with an IR camera, setting up a camera, providing location information, reporting, annotating, adding voice or text, identifying, printing, and providing PC communications. In the most preferred embodiments, results of the performance of these inspection processes are communicated back to the workstation.

Figure 1:
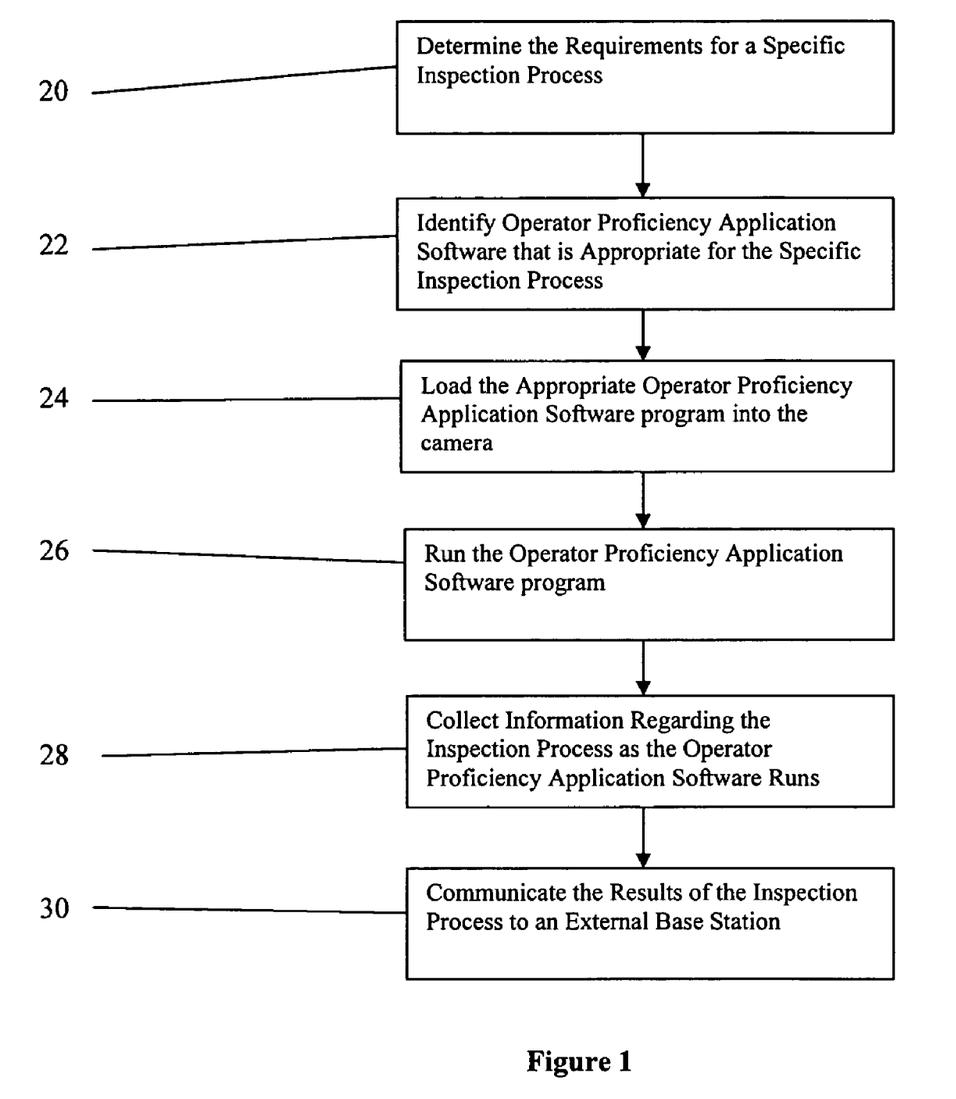
FIG. 1 is a flowchart of the environment for conducting an inspection process and a method for conducting an inspection process according to the invention.

FIG. 1 depicts an overview of a typical environment for inspection and identifies steps incorporated in some embodiments of operator proficiency application software methods that are used for directing an inspection process. Some of the steps are often internal to the inspection process and some steps are often external to (not a part of) the process. Step 20 is an element that is often external to the process and consists of determining the requirements for a specific inspection process. Typically this step is performed by engineers or technicians who are familiar with the item to be inspected and systematically identify factors that need to be included in the process. Step 22 is an element that is sometimes external to the process. It constitutes identifying operator proficiency application software that is appropriate for the specific inspection process identified in Step 20. Step 22 is also may be performed manually by engineers or technicians, although in preferred embodiments the identification of operator proficiency application software is accomplished automatically by applications software that controls a software repository. Step 24 is generally an internal step that consists of loading the appropriate operator proficiency application software program into the programmable camera that is going to be used for the inspection process. In some cases, more than one operator proficiency application software program is loaded into the programmable camera. Step 24 is typically performed by the operator selected to conduct the specific inspection process. Step 26 is also generally an internal step consisting of running the operator proficiency application software program, and is conducted by the operator. Step 28, which is used in some embodiments, consists of collecting information as the operator proficiency application software program is running. Preferably the collection of information is accomplished automatically by the operator proficiency application software program. Step 28 is used primarily where information regarding the results of the inspection process must be collected. Step 30 is communicating the results of the inspection process to an external system, such as a base station or network server. Step 30 is used in some embodiments where Step 28 has been employed, to report the results of the inspection process.

An important consideration regarding FIG. 1 is that it provides the most preferred sequence of steps for using a single operator proficiency application software program. In some embodiments several operator proficiency application software programs may be used, and in such embodiments one step may be repeated several times before the next step is started, or some combinations of steps may be repeated as a loop, and in some embodiments a step may be eliminated. For example, several operator proficiency application software programs may be loaded before the first operator proficiency application software program is run. Alternately, one operator proficiency application software program may be loaded and run before a second operator proficiency application software program is loaded and run. As another example, one operator proficiency application software program may be loaded and run, and information collected regarding the inspection process, and the results of the inspection process communicated to an external base station, and then the entire sequence repeated for a second operator proficiency application software program. Alternately, multiple operator proficiency application software programs may be loaded with each one being run, having data collected, and being reported before the second operator proficiency application software program being run, having data collected, and being reported. Virtually any combination of these sequences is possible when using several particular operator proficiency application software programs.

One part of many embodiments is providing in-camera operator training, validation, and certification. Infrared inspection often involves expensive and dangerous applications such as power transmission and electrical delivery systems. A mistake during the inspection process may result in operator injury or death, or it could lead to property damage or production outage. Those are some of the justifications for defining levels of operator certification and associated training and instruction in preparation for the equipment examinations.

Each inspection process entails a number of different aspects. Among the different aspects are proper procedures, safety warnings, location information, and equipment information including equipment identification, equipment functions and characteristics, equipment normal and abnormal thermal signatures, and information about auxiliary tests (besides infrared thermography) that may be useful in assessing the equipment's performance.

Generally, modem infrared cameras are easily packed into a suitcase and shipped from one location to another, and may be interchanged from one operator to another. While almost anyone can power-up an infrared camera and view the visible image it produces, specific operator skills are needed in advance of "certified inspections." Such skills may be acquired through a process of training or certification testing.

In some embodiments presented herein, the training and certification is accomplished using media on-board the IR camera system by installing an inspection training application software routine on-board the camera. Such software may, for example, provide audio-visual information such as a Microsoft® Powerpoint® presentation with audio information. Alternately, an Adobe® Acrobat® presentation may be executed using the portable display without audio. The inspection training application software routine training course may include interactive features so that the operator receives and responds to fixed sequential or variably branched prompts.

In preferred embodiments the inspection training application software routine provides training information that includes procedural instructions, such as how to remove the cover from a piece of equipment, or how to set the operational mode of a piece of equipment so that its thermal profile can properly be inspected. In another form, the training information may be a safety class that the operator completes at the outset of a new survey. The safety class may include a safety warning instruction such as "Use the portable AC hipot tester to make certain the power is off before proceeding!" In general, the training information provides at least one description of at least one aspect of an inspection process.

As subsequently described in further detail, the inspection training application software routine may interact with a simple or a complex validation or certification test as needed to assure satisfactory completion of necessary requirements for performance, safety, or effectiveness.

Many embodiments incorporate an operator validation application software routine. The concept of validation as used herein is also called by many other names including but not limited to the following list: certify or certification, verify or verification, validate or validation, authenticate or authentication, qualify or qualification, notary or notarization, accredit or accreditation, etc. The purpose of the operator validation application software routine is to validate that the operator is sufficiently knowledgeable about a particular aspect of an inspection process. To do this, the validation application software will pose to the operator one or more validation questions associated with that aspect of the inspection process and indicate the operator's responses. Examples of validation questions would be questions directed at ascertaining the operator's understanding of classifications of findings, or questions designed to determine the operator's performance level. Other validation questions may relate to safety issues, training records, location familiarity, or equipment familiarity. The operator answers these questions and the application software collects the responses. The validation questions together with the operators responses constitute validation information that assess the operator's qualifications to perform at least one aspect of an inspection. Validation information includes at least one validation question associated with at least one aspect of an inspection process and at least one correct answer to at least one validation question is generally required to confirm that an operator is sufficiently knowledgeable about a particular aspect of an inspection process. In preferred embodiments, acceptable validation information is required before authorizing an inspection, i.e., before the application software will permit the operator to conduct the inspection.

Some inspections require certified inspectors. To accommodate this requirement, in some embodiments the application software routines include the collection of certification information. This involves having the application software pose certification questions to the operator, where the certification questions are questions associated with at least one aspect of the inspection process. The number of certification questions posed is sufficient to certify the operator for at least one aspect of the inspection process if a sufficient number of the operator's responses are correct. The certification questions together with the operators responses constitute certification information that is used by a certification algorithm to assess the operator's qualifications to perform an inspection. Certification information includes a plurality of certification questions, and the operator's responses to the plurality of certification questions, and a determination of the operator's certification. The determination of the operator's certification status is made by using the certification algorithm to calculate whether the number of the operator's correct responses is sufficient to certify the operator for at least one aspect of the inspection process. The certification information then identifies which aspect of the inspection process the operator is certified to perform. In preferred embodiments, acceptable certification information is required before authorizing an inspection, i.e., before the application software will permit the operator to conduct the inspection.

Another element of some embodiments is the automation of the area survey process through the use of an on-board survey template application software routine. An area survey is generally a randomized and unstructured process. Most people are naturally inclined to use an infrared inspection system like they would their human eyes during a visual inspection. They enter a new location gaze around everything in the vicinity to get a big picture before approaching one or another item for closer inspection. A person's gaze takes in literally thousands of bits of information very rapidly. Without much effort the operator quickly discerns where problems may be found because extreme or unusual images are easily distinguished with the eye. Sometimes before you even realize what piece of equipment you are looking at, you know that something is wrong.

In the most preferred embodiments, the survey template application software routine automates the process of area survey inspection several ways. First, the automated thermographic inspection process is fault-centered, rather than equipment centered. This means that the operator is prompted to identify and to report problems that are observed regardless of where or when they are observed. In preferred embodiments the survey template application software routine is also exception based which means that records are established for exceptions and little is documented unless there is a problem. To accomplish this, exception identification information is provided to the operator. The exception identification information may include a list of locations to check for abnormal conditions, a list of problems that are often encountered with a particular type of equipment, a fault-tree analysis diagram, a trouble-shooting guide, a list of previously-identified problems with a particular piece of equipment, and so forth.

In order to perform an area survey, preferably the user employs a portable infrared system with on-board computer that is programmed using the survey template application software routine to guide him or her through the area survey. This involves defining area survey parameters for different aspects of the survey process.

Generally, one of the first area survey parameters of the survey template application software routine is specifying an area to be surveyed. This can be a descriptive designator such as "Motor Control Center CT345" or it may simply be sequential area "3." Next the operator is instructed to search for characteristic faults that are sometimes found in that vicinity. When a fault is found, the operator is taught to log the fault, add appropriate information, take visible and infrared images as needed, and provide an interpretation of the nature of the fault.

Another element of the survey template application software routine is defining area survey parameters that are to be identified when a fault is found in an area. Generally the first area survey parameter that the operator identifies is the specific location or equipment where the fault is found. This may be accomplished using a visual method, such as reading a nameplate or recognizing the machine. It may also be accomplished using a tagging system such as barcode, radio-frequency identification, touch-button identification, or even a global positioning system or other general locator. In any case, the objective is to document the specific place where the fault is found.

Figure 2:
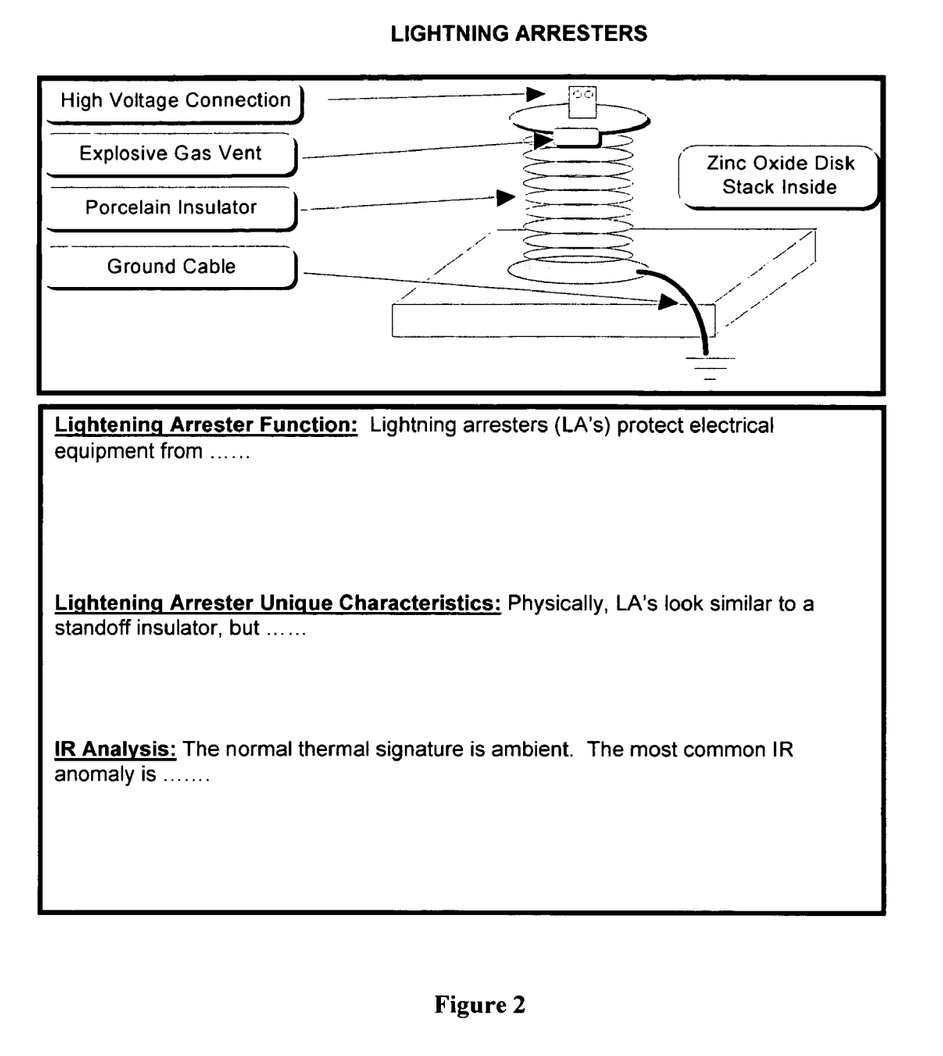
FIG. 2 is a template of an area survey parameter according to the invention.
Figure 3:
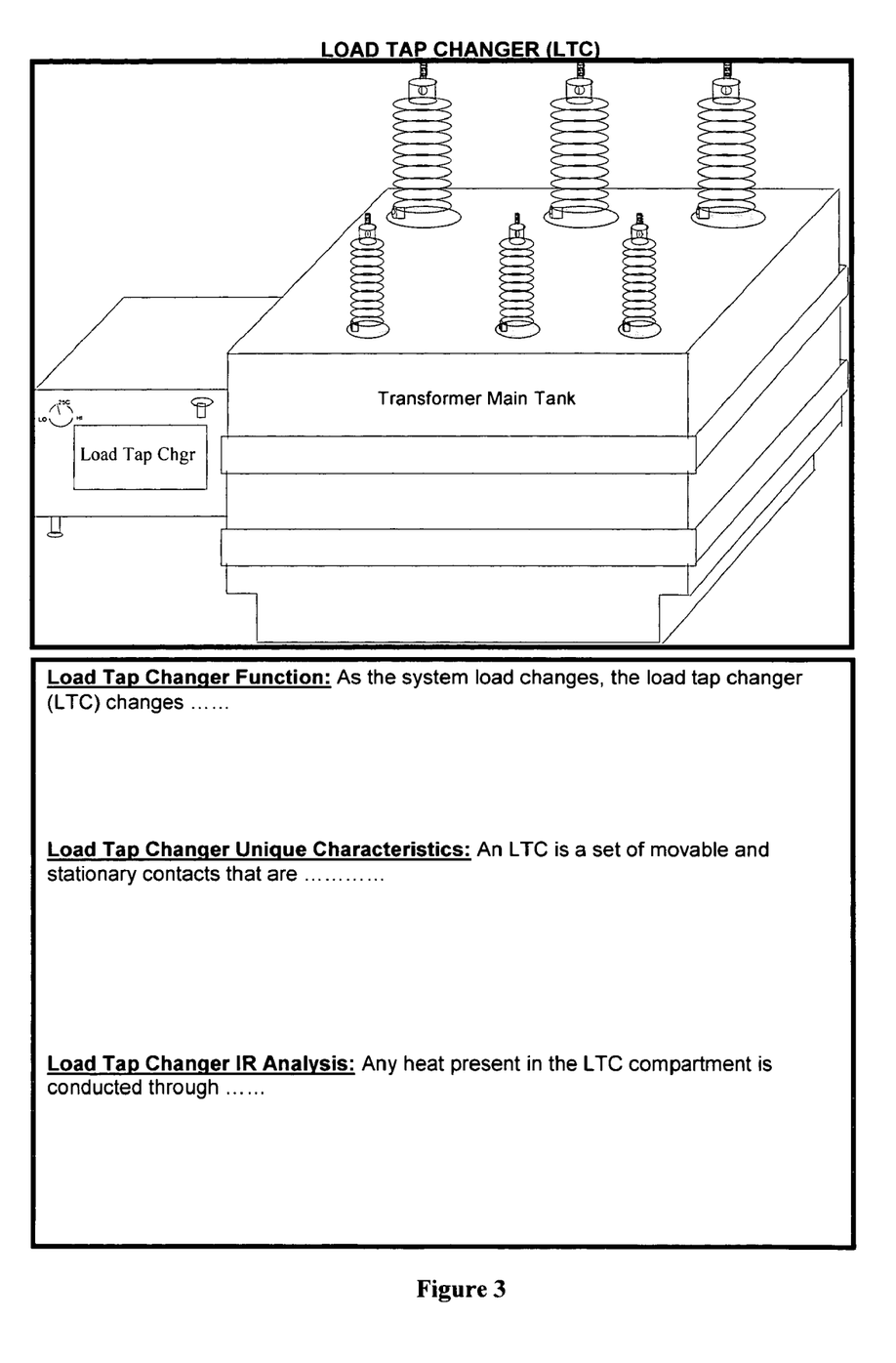
FIG. 3 is a template of a different area survey parameter according to the invention.
Figure 4:
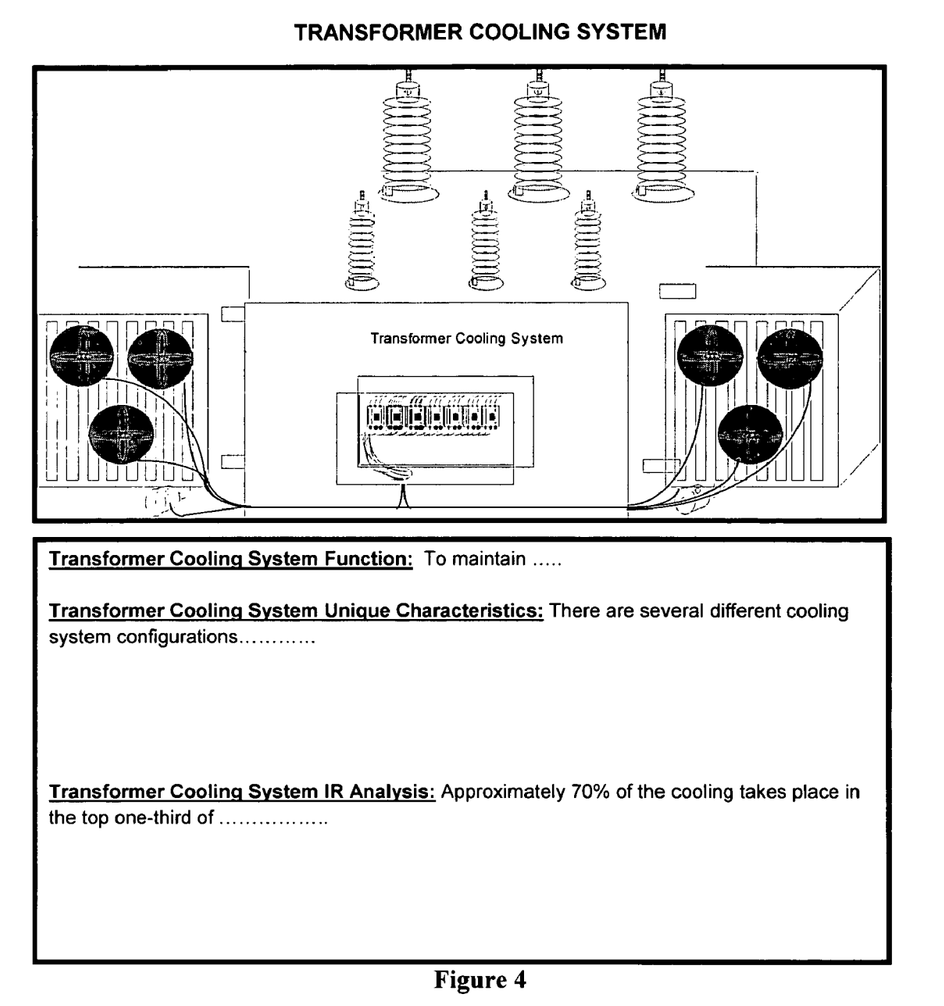
FIG. 4 is a template of a different area survey parameter according to the invention.

In preferred embodiments, the survey template application software routine helps lesser-trained operators understand the types of equipment on which unusual findings are often observed. FIGS. 2, 3, and 4 are examples of templates used to assist an operator in performing an inspection. In preferred embodiments, both the graphical and the textual information are presented on the viewing screen of the portable infrared camera system. Typically some scrolling of the information on the screen is required. For example, the full text in FIG. 2 may include the information presented in Table 1, the full text in FIG. 3 may include the information presented in Table 2, and the full text in FIG. 4 may include the information presented in Table 3.

TABLE 1

| | |
|---|---|
| Lightning Arrester Function: | Lightning arresters (LA's) protect electrical equipment from damaging surges from lightning. The location of an LA in the circuit will help to distinguish it from similar looking components, such as standoff insulators. The LA is usually connected to the bus with a section of cable that provides no physical support of the bus. It is usually the first component in the circuit. In other words, when an incoming line enters a substation yard, the first component on that line is usually the LA. The same holds true for the incoming lines to a transformer. |
| Lightning Arrester Unique Characteristics: | Physically, LA's look similar to a standoff insulator, but with several minor differences. The LA has a large ground cable connected at the bottom and it runs down the structure that connects to the station ground. Sometimes a fault meter is installed in this ground cable to record any lighting-to-ground events. |
| IR Analysis: | The normal thermal signature is ambient. The most common IR anomaly is a high resistance connection at the top of the bushing, either in the pad or bushing adapter. The adapter is a separate piece that screws on to the main stud, and looks like a larger version of the main stud. Be aware that the adapter-to-stud connection can fault and cause heating. A micro ohm reading can be taken to pinpoint the high resistance and to confirm the repair. |

TABLE 2

| | |
|---|---|
| Load Tap Changer Function: | As the system load changes, the load tap changer (LTC) changes tap position, which changes the voltage output of the transformer. This maintains the proper operating voltage to the system being fed. Consider the LTC to be an oil circuit breaker that gets an enormous amount of work. It is driven by a motor and mechanical linkage. In most cases the motors are in an adjacent cabinet; but in some of the older units the motors are located inside the LTC compartment and are operated completely submerged under the oil. |
| Load Tap Changer Unique Characteristics: | An LTC is a set of movable and stationary contacts that are enclosed in a separate compartment and attached to the main tank of a transformer. The LTC compartment is oil filled and either vented to the atmosphere, sealed or gas blanketed. Flexible leads from the transformer section enter the LTC compartment through holes in an insulated board between the two compartments. The holes have oil seals around the cables to keep the LTC oil separate from the main tank oil. These seals can be damaged by heat and will allow leakage of oil between compartments. The cables connect the transformer winding to the LTC. |
| Load Tap Changer IR Analysis: | Any heat present in the LTC compartment is conducted through the insulation board from the transformer section of the unit. Under normal conditions the LTC compartment will be 5 C. to 10 C. cooler than the main tank at the same elevation. Even a 1 C. rise should be investigated. The LTC is not a heat source under any load condition. |

In these examples the templates are used to describe area survey parameters regarding an item of equipment that is being inspected in terms of its function, its distinctive physical attributes, and its infrared image characteristics. For example, an operator who is new to substation monitoring can use the in-camera information depicted in FIG. 2 and FIG. 3, which in whole or part is displayed on the camera's viewing screen, to determine if he is looking at a lightning arrestor or a load tap changer. As another example, when an inexperienced operator using the IR inspection system is performing a survey and encounters an anomaly in a Transformer Cooling System; he or she may bring up in the portable system the descriptive information of FIG. 4. From this description the operator can look for suggested fault conditions. In this case if the operator finds cooling fans operating in reverse and one cold radiator is cold, then he can log fault conditions requiring corrective action in both operation and failure prediction categories as described in the following sections.

Figure 5:
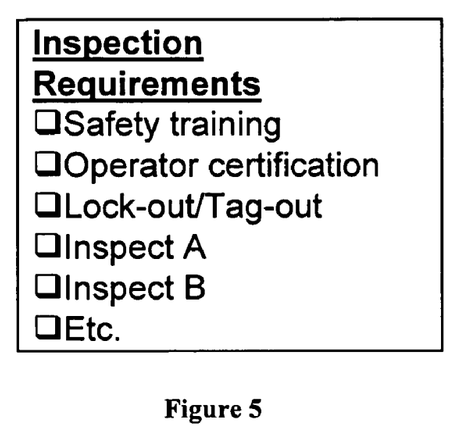
FIG. 5 is a schematic diagram of a template of a different area survey parameter according to the invention.
Figure 6:
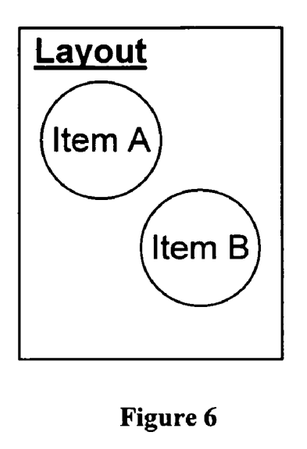
FIG. 6 is a schematic diagram of a template of a different area survey parameter according to the invention.
Figure 7:
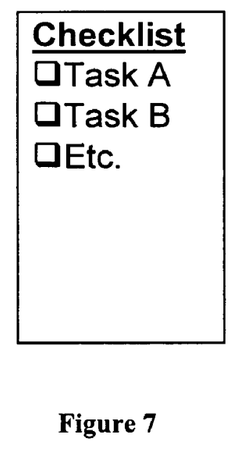
FIG. 7 is a schematic diagram of a template of a different area survey parameter according to the invention.
Figure 8:
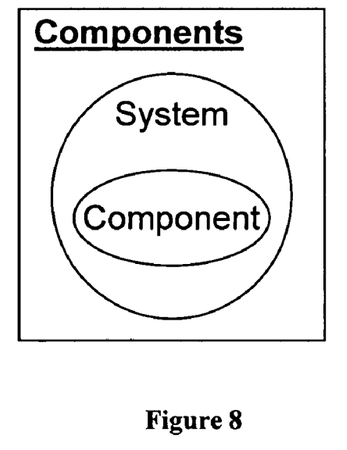
FIG. 8 is a schematic diagram of a template of a different area survey parameter

FIG. 5 presents an alternate example of a inspection template that is used in some embodiments of a survey template application software routine. This template presents a sequence of inspection requirements that is relevant to a particular inspection process. FIG. 6 presents a further alternate example of a template, where the physical layout of two items of equipment are portrayed. FIG. 7 depicts a checklist form of a template. FIG. 8 illustrates a template showing the location of a particular component in a system.

In preferred embodiments, the application software requires confirmation that the latest approved templates are loaded into the camera before the application software will permit the operator to conduct the inspection. Such confirmation may be obtained by requiring the operator to assert that the templates are up-to-date or by uploading the templates prior to conducting the inspection, or by some other verifiable method. The term "prior to" means an interval of time that is sufficiently close to the start of the inspection, such that there is reasonable certainty that the application software routine (e.g. the templates) are a currently valid version. The appropriate interval of time is dependent on such factors as how frequently the software is updated and how critical the inspection is.

In preferred embodiments, the automated thermographic inspection process resolves complex data into practical and understandable results (i.e., findings) using a survey results application software routine. Generally, a single infrared survey involves countless temperature measurements taken from thousands of components. The amount of data is immense. Without the automated thermographic inspection process, a successful inspection depends upon human operators being vigilant and consistent in determining which temperature measurements are worth documenting and deciding how to report them. That process leaves room for inconsistency, missed findings, and errors.

Preferred embodiments employ a survey results application software routine for resolving complex data into one of a plurality of dissimilar classifications. In one embodiment, the approach is to classify all findings as "failure predictions," "operational conditions," or "design characteristics." Fault lists may be created with each fault categorized under one or more of these classifications. For example, a relatively hot connection on a circuit breaker panel may indicate that a failure is in progress or may simply indicate that the power is flowing through that connection. If the connection is failing, the infrared inspection system can be used to monitor the progression of the failure over time and help if the condition is incipient or near late-stage catastrophic failure. It is appropriate to use multiple measurements over time to trend and thereby predict catastrophic failure. On the other hand, if the heat is simply due to power being turned on (e.g., normal operation), that fact is considered and may or may not need to be documented.

Some implementations instruct the operator to further assess and document certain operational conditions to either verify normal operation or alert to unexpected operation. Anomalies in operating conditions are quite different from anomalies associated with failure in progress, and should be classified differently.

As previously indicated, in some embodiments the process is used to document observed design or quality factors. These factors are different from either failure predictions or operational conditions. For example, the insulation system in an exterior wall is supposed to have R-12 insulation. However, an infrared survey on a cold night outside the building may reveal far lower insulation is actually in place for one section of a the wall. In this case the specification or design or quality was below acceptable standard.

In preferred embodiments, one step in the process of resolving complex data involves grouping faults or findings into three generally exclusive and dissimilar categories such as "failure," "operational," and "design." Another step is the assignment of alarm or severity level for each category. Such characterizations are called grading levels, and typically this is done by assigning one of three or five different grading levels for each finding category. One implementation may describe three grading levels, e.g., "normal," "alert," and "fault." Five grading levels may be described as "Normal ," "Low Alert," "High Alert," "Low Fault," and "High Fault." Human action or intervention is recommended when the condition reaches a particular level such as "Fault" on the three-level method or "High Fault" on the five-level method. Color is often used to in association with alarm or severity status. Representations used in some embodiments are depicted in Table 4.

TABLE 4

| Alarm or Severity | Significance | Color |
| --- | --- | --- |
| High Fault | The problem is extreme. | Red |
| Low Fault | Problem identified needing human action to be taken | Red |
| High Alert | Warning of impending action required | Yellow |
| Low Alert | Differences are noticed | Yellow |
| Normal | Nothing unusual to report | Green |

Figure 9:
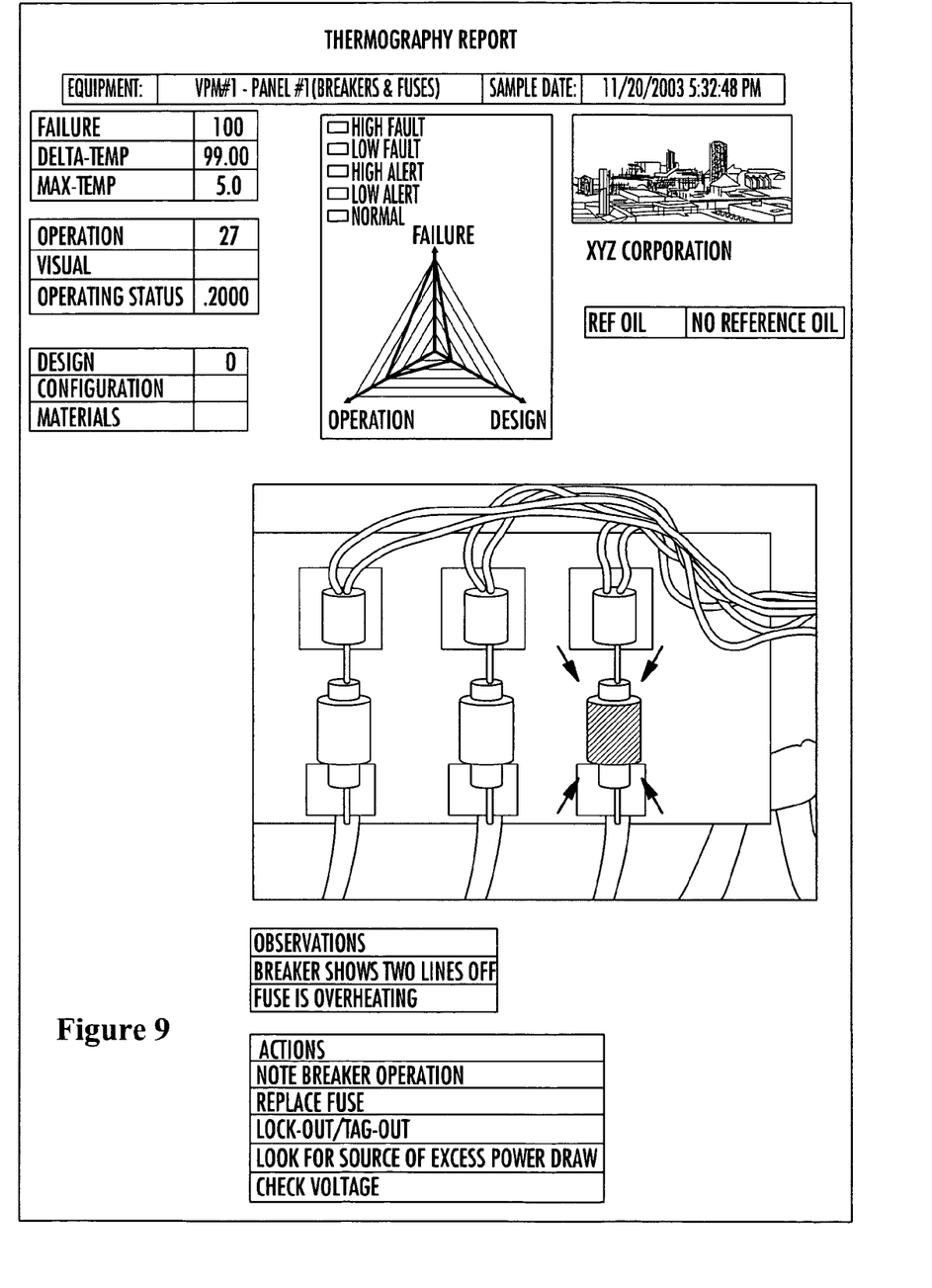
FIG. 9 is an example of one page of a report produced according to the invention.

In preferred embodiments, one may chose to graphically represent the status values for failure, operation, and design. This could be done different ways such as in the form of a bar graph or multi-dimensional representation. In a simple embodiment, the results are portrayed as a numerical dataset. For example, the results could be (1,4), (2,0), (3,2), where the first number in the set represents the category and the second number represents the grading level. In the most preferred embodiments a multi-vector graphical representation is used. For example, in a duo-vector representation, one category may be depicted on the abscissa and a second category depicted on the ordinate of orthogonal axes. The severity level may be depicted as increasing numerical values starting at the intersection (origin) with levels of alarm or severity increasing as the distance from the origin increases. A tri-vector representation adds a third dimension to the graphical representation. An example of a tri-vector graphical representation is shown in FIG. 9, which is discussed in detail later.

It is possible and practical to integrate findings from alternate sources in addition to infrared inspection information into a multi-category format. For example, one may record observations including process variables such as temperature, pressure, and flow conditions while accomplishing infrared surveys. These operational conditions can contribute to the overall findings. The same can be applied to information or data gained from associated condition monitoring information such as vibration analysis or ultrasonic analysis or oil analysis information. All of these can be interpreted in a form similar to that shown in the Table 4. Those findings can be accumulated along with infrared observations during an infrared survey.

Generally, all of the findings associated with each classification category are considered in the assignment of an overall severity level for each category (e.g., for "failure," "operation," and "design"). Normally, when multiple parameters or anomalies in one category are considered, the highest one determines the overall level. However, to avoid nuisance alarming, false negatives, and false positives; consideration may be given to multiple measurements, data, and information from various sources when determining the overall values for each of these three categories. By resolving the complex data from infrared surveys into these three dimensions (categories) and assigning a grading level to each, anyone who reads the report can easily interpret the significance of the findings.

To further facilitate reporting, a preferred embodiment incorporates a portable system that is carried back to the base station periodically to download information and upload historical and other information. The invention may also be applied to accomplish the same end result using wireless communication with a host database or using a thin-client or other "dumb" terminal application. If the portable system is robust enough, some or all of the functions may be performed entirely on a computer system imbedded in the portable IR system. On the other hand, many of the functions described may be accomplished using download-only communication with the portable system.

In a preferred embodiment, the survey results application software routine recommends a follow-on step to the operator if a pre-defined threshold is crossed. Logical observations and actions are initiated based upon findings or anomalies detected during the survey. A threshold may be set for each category based upon a grading level. The follow-on step may be a recommended additional observation, an additional action, an additional recording, or some other activity that is logically suggested by crossing the threshold for a specific category. For example, the observation that an electrical coupling is exceptionally hot may trigger recommendation for these logical actions:

visually inspect coupling,
visually photograph coupling,
CAUTION! LOCK-OUT TAG-OUT BEFORE APPROACH!.

Figure 10:
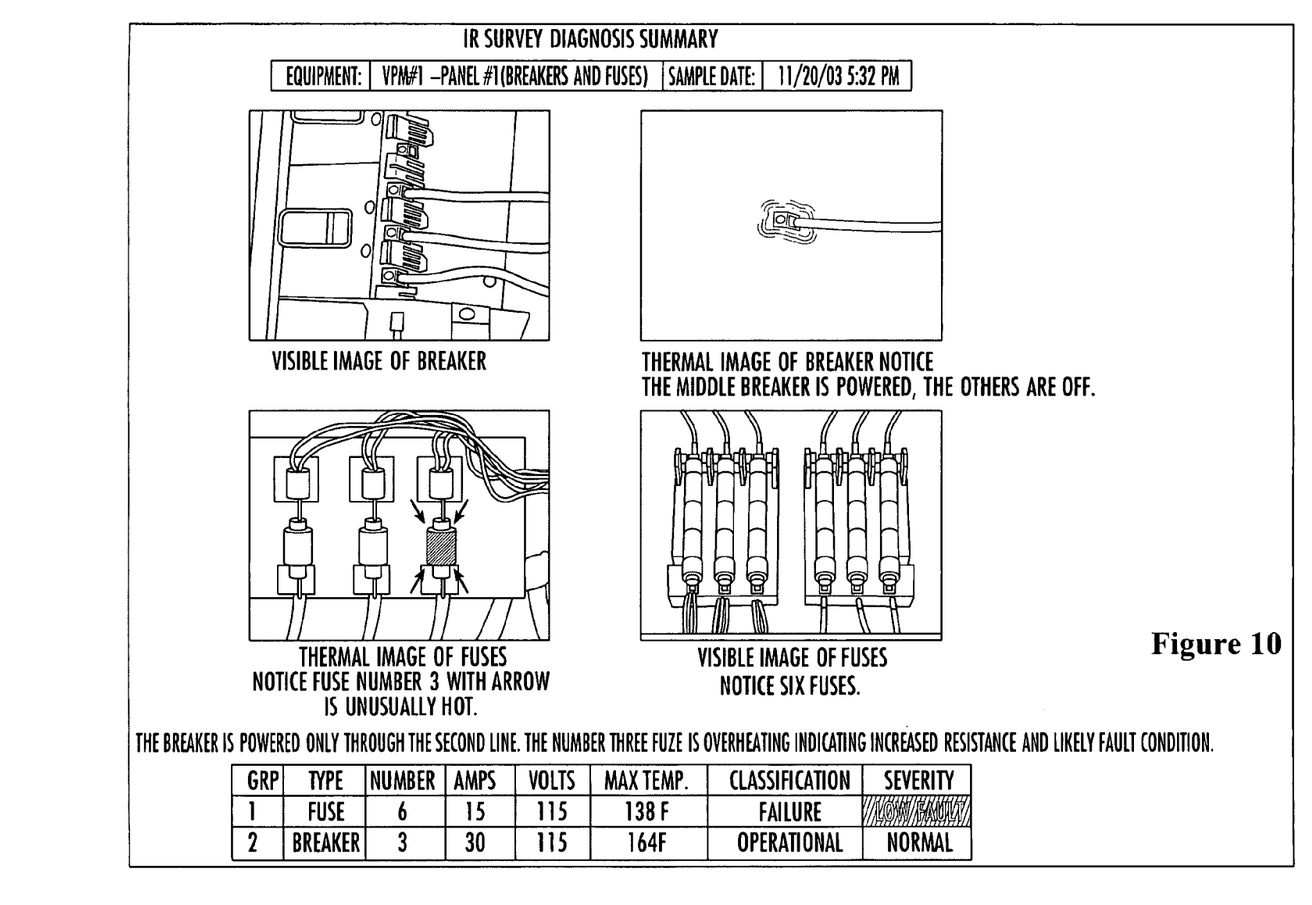
FIG. 10 is a an example of one page of a report produced according to the invention.

One benefit of most preferred embodiments is an automated reporting process that is far beyond what could be done earlier. Adobe® PDF or MS Word® or other type reports may be fully formatted in the portable IR system at the completion of the area survey. Two examples of one page of a report are provided in FIGS. 9 and 10.

Figure 11:
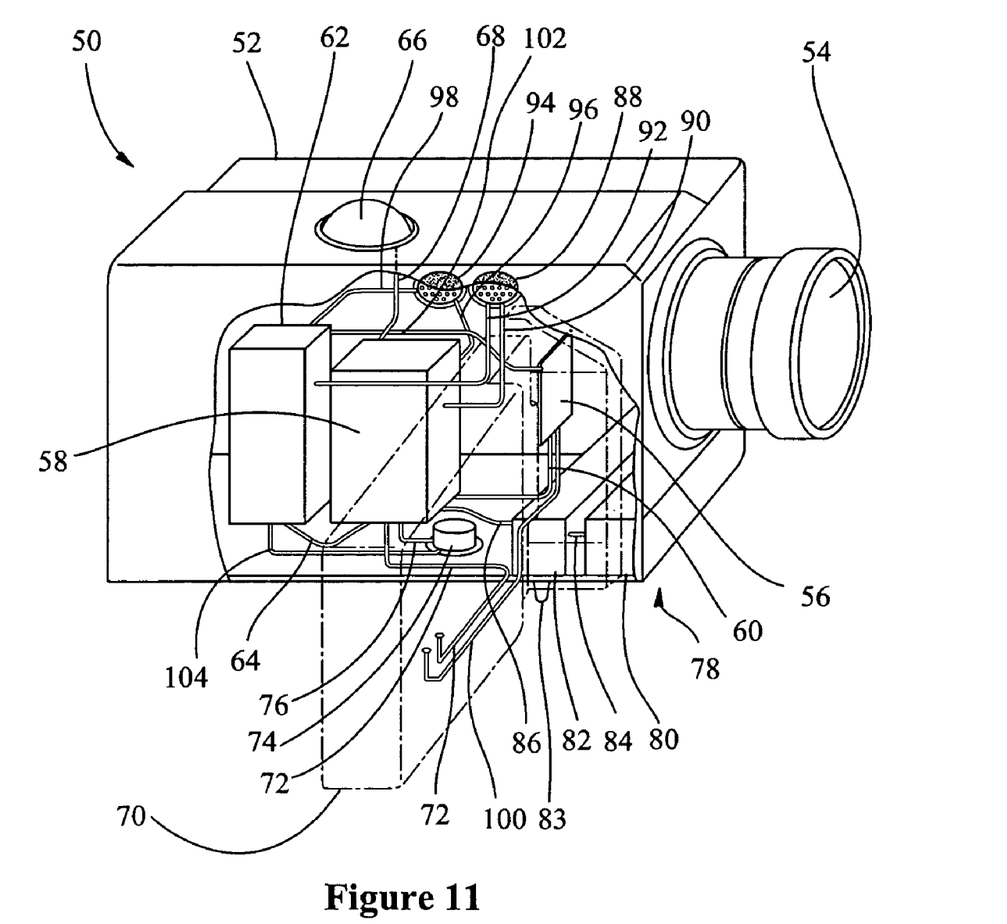
FIG. 11 is diagrammatic illustration of an infrared inspection camera according to the invention.

A preferred embodiment of the automated thermographic inspection system is implemented in a hardware configuration as illustrated in FIG. 11 where an inspection camera 50 is depicted in a partial cutaway schematic representation. The inspection camera 50 has a housing 52 with a lens 54 on one surface of the housing 52. The lens 54 focuses electromagnetic radiation onto an imaging array 56 located in the camera 50. In the most preferred embodiments, lens 54 is an infrared lens and imaging array 56 is an infrared focal plane array. For some embodiments, particularly embodiments involving multi-vector representation of a plurality of dissimilar classifications, lens 54 may be transmissive to either visible light or infrared photons or to both, and the imaging array 56 may be a sensitive to either visible light or infrared photons or to both. A microprocessor 58 accepts image data from the image array 56 through interface 60. Microprocessor 58 includes microprocessor operating system software and application software. In many embodiments microprocessor 58 includes a central processing unit (CPU), a memory controller, at least one input/output (I/O) transceiver, at least one clock generator, buffers, communication buses, and a voltage regulation and power distribution subsystem. Microprocessor 58 accesses a data storage memory 62 through an interface 64. A user input device, such as a thumb-mouse 66, is connected to microprocessor 58 through interface 68. A display 70 is driven by microprocessor 68 through interface 72. Preferably a communications adapter 74 is connected to microprocessor 68 through interface 76 to permit uploading and downloading of information to and from the data storage memory 62. Most preferably, communications adapter 74 is a wireless communication link.

The embodiment depicted in FIG. 11 includes a power source 78 that includes a battery 80 connected to an electronic power supply 82 through interface 84. Power source 78 is part of the power distribution system for inspection camera 50. Power supply 82 includes an externally accessible switch 83 for turning inspection camera 50 off and on. Power supply 82 is connected to microprocessor 58 through interface 86. In some embodiments microprocessor 58 distributes power through interfaces to other components using its voltage regulation and power distribution subsystem. In some embodiments interface 86 includes a voltage bus that provides at least a portion of the power distribution to other components of inspection camera 50 through interfaces not depicted in FIG. 11. In some embodiments battery 80 is a rechargeable battery. In some embodiments an alternate to battery 78 is used, such as an ac/dc voltage transformer that is connected between the power supply 82 and standard distributed utility ac power. In a further alternate embodiment power source 78 may comprise an external electrovoltaic source of energy that connects directly to interface 86 thereby eliminating battery 78 and power supply 82.

In the most preferred embodiments, inspection camera 50 is a portable infrared inspection camera system that is easily hand-carried by an operator. The housing 52 represents this hand-carried package. In alternate embodiments there are advantages to having the ability to separate components shown in FIG. 11. For example one may remove the display 70 from the rest of the items in housing 52 using a cable or wireless interface. In another example one may use a cable or wireless interface 68 or separate the lens 54 and imaging array 56 from the remainder of the items in housing 52. In a third example, one may use a cable or wireless interface to connect the user input device (e.g., thumb-mouse 66, or a keyboard) to the inspection camera 50. In such cases the connection to the inspection camera 50 is preferably made through communications adapter 74. In a fourth example, one may place the storage memory 62 on an external device, again using cable or wireless interface to transmit data to and from the storage memory. These and other configurations for separating and combining functions portrayed in FIG. 11 are relevant to various alternate embodiments.

Continuing with FIG. 11, certain embodiments may include a speaker 88 for audible communication from the inspection camera 50 to the operator. Speaker 88 is shown connected to microprocessor 58 through interface 90. In some embodiments, speaker 88 may include sufficient integral electronics such that it is optionally connected to data storage memory 62 through interface 92. Some embodiments may include a microphone 94 as a user input device or for processing or recording voice and other audio information. Microphone 94 is shown connected to microprocessor 56 through interface 96. In some embodiments microphone 94 may include sufficient integral electronics such that it is optionally connected to data storage memory 62 as shown through interface 98. In some configurations image array 56 may also include sufficient integral electronics such that it is optionally connected to display 70 through interface 100 or optionally be connected to data storage memory 62 as shown through interface 102. Also in some embodiments data storage memory 62 or communications adapter 74 may include sufficient integral electronics such that they are connected through interface 104.

In preferred embodiments the application software in microprocessor 58 comprises operator proficiency application software that provides training information through display 70. In some embodiments the operator proficiency application software collects validation information using information stored in data storage memory 62 and input provided by an operator using an input device such as thumbmouse 66. In some embodiments the operator proficiency application software collects certification information using information stored in data storage memory 62 and input provided by an operator using an input device such as thumbmouse 66.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for directing an inspection process using a programmable infrared camera, the method comprising
   (a) loading the programmable infrared camera with a survey template application software routine where the survey template application software routine describes at least one aspect of the inspection process,
   (b) running the survey template application software routine to instruct an operator to inspect the vicinity of an area and to guide the operator through the at least one aspect of the inspection process,
   (c) where loading the camera with a survey template application software routine comprises uploading at least a portion of the survey template application software routine from a software repository, and
   (d) where using a programmable infrared camera comprises using a programmable infrared camera with a wireless communication link and further comprises wirelessly uploading at least a portion of the survey template application software routine using the wireless communication link.

2. A method for directing an inspection process using a programmable infrared camera, the method comprising
   (a) loading the programmable infrared camera with a survey template application software routine where the survey template application software routine describes at least one aspect of the inspection process,
   (b) running the survey template application software routine to instruct an operator to inspect the vicinity of an area and to guide the operator through the at least one aspect of the inspection process, and
   (c) identifying a location within the vicinity of the area using a global positioning system.

3. A method for directing an inspection process using a programmable infrared camera, the method comprising
   (a) loading the programmable infrared camera with a survey template application software routine where the survey template application software routine describes at least one aspect of the inspection process, and
   (b) running the survey template application software routine to instruct an operator to inspect the vicinity of an area and to guide the operator through the at least one aspect of the inspection process, wherein the running step further comprises running the survey template application software routine to display a checklist.

4. A method for directing an inspection process using a programmable infrared camera, the method comprising
   (a) loading the programmable infrared camera with a survey template application software routine where the survey template application software routine describes at least one aspect of the inspection process,
   (b) running the survey template application software routine to instruct an operator to inspect the vicinity of an area and to guide the operator through the at least one aspect of the inspection process, and
   (c) uploading historical information to the programmable infrared camera.

5. A method for directing an inspection process using a programmable infrared camera, the method comprising
   (a) loading the programmable infrared camera with a survey template application software routine where the survey template application software routine describes at least one aspect of the inspection process,
   (b) running the survey template application software routine to instruct an operator to inspect the vicinity of an area and to guide the operator through the at least one aspect of the inspection process,
   (c) running the survey template application software routine to prompt the operator to perform steps in an infrared survey, and
   (d) creating a record of that survey.

* * * * *